United States Patent [19]

Massingill

[11] Patent Number: 4,579,959
[45] Date of Patent: Apr. 1, 1986

[54] OLEFINIC EPOXY COMPOUNDS

[75] Inventor: John L. Massingill, Lake Jackson, Tex.

[73] Assignee: The Dow Chemical Company, Midland, Mich.

[21] Appl. No.: 700,155

[22] Filed: Feb. 11, 1985

[51] Int. Cl.$^4$ ............................................. C07D 303/12
[52] U.S. Cl. .................................... 549/555; 549/560; 526/273
[58] Field of Search ................ 549/555, 560; 526/273

[56] References Cited

U.S. PATENT DOCUMENTS

| | | | |
|---|---|---|---|
| 2,946,825 | 7/1960 | Monroe et al. | 549/555 |
| 2,986,569 | 5/1961 | Monroe et al. | 549/560 |
| 3,377,406 | 4/1968 | Newey et al. | 260/637 |
| 3,420,914 | 1/1969 | May | 260/837 |
| 3,450,613 | 6/1969 | Steinberg | 204/159.15 |
| 3,637,618 | 1/1972 | May | 260/837 R |
| 3,736,289 | 5/1973 | Marshall | 260/837 R |
| 3,753,755 | 8/1973 | Olson | 117/3.1 |
| 3,793,398 | 2/1974 | Hokamura | 260/835 |
| 3,873,638 | 3/1975 | Olson | 260/837 R |

*Primary Examiner*—Paul R. Michl
*Assistant Examiner*—Alex H. Walker
*Attorney, Agent, or Firm*—James G. Carter

[57] ABSTRACT

Olefinic epoxy compounds are prepared by reacting a material containing at least one terminal —C≡CH group with an epihalohydrin followed by dehydrohalogenation. The materials are useful as halogen scavengers in the preparation of coatings, castings, laminates, composites, and the like.

6 Claims, No Drawings

OLEFINIC EPOXY COMPOUNDS

BACKGROUND OF THE INVENTION

The present invention pertains to compounds having at least one olefinic unsaturated group and at least one glycidyl ether group.

Unsaturated epoxy compounds such as glycidyl methacrylate have been employed in halogenated polymers as acid scavengers however, because of the ester groups, they are hydrolytically unstable.

It has now been discovered that compounds having a terminal acetylenic group react with an epihalohydrin by addition to the acetylenic group to form an ethylenic halohydrin ether which can be dehydrohalogenated by conventional means to form an ethylenically unsaturated glycidyl ether. Glycidyl ethers are much more hydrolytically stable.

SUMMARY OF THE INVENTION

One aspect of the present invention pertains to compounds represented by the formula

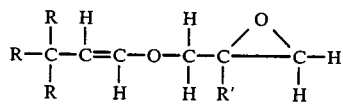

wherein each R is independently hydrogen, a hydrocarbyl group having from about 1 to about 12, preferably from 1 to about 6 carbon atoms, a glycidyl ether group or a glycidyl ether substituted hydrocarbyl group having from 4 to about 8, preferably from 4 to about 6 carbon atoms or two of such R groups can be combined to form a cyclic structure and wherein R' is hydrogen or an alkyl group having from 1 to about 3 carbon atoms.

The present invention also pertains to cured compositions of the aforementioned compounds having two or more glycidyl ether groups.

DETAILED DESCRIPTION OF THE INVENTION

Suitable materials having at least one terminal acetylenic group which can be employed herein include, for example, those represented by the formula

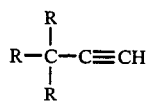

wherein each R is independently hydrogen, a hydrocarbyl group having from 1 to about 12, preferably from about 1 to about 6 carbon atoms, a hydroxyl substituted hydrocarbyl group having from about 1 to about 12, preferably from about 1 to about 6 carbon atoms or two of such R groups can be combined to form a cyclic structure.

Particularly suitable such acetylenic compounds include, for example, 3,5-dimethyl-1-hexyne-3-ol, methyl acetylene, butylene acetylene, acetylene, mixtures thereof and the like.

Suitable epihalohydrins which can be employed herein include, for example, those represented by the formula

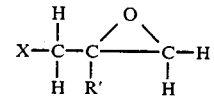

wherein R' is hydrogen or an alkyl group having from 1 to about 3 carbon atoms and X is a halogen.

Particularly suitable epihalohydrins include, for example, epichlorohydrin, epibromohydrin, epiiodohydrin, methylepichlorohydrin, methylepibromohydrin, methylepiiodohydrin, mixtures thereof and the like.

The reaction between the acetylenic compound and the epihalohydrin is usually conducted in the presence of a phase transfer catalyst such as, for example, quaternary ammonium compounds, quaternary phosphonium compounds, sulfonium compounds, crown ethers, mixtures thereof and the like.

Particularly suitable quaternary ammonium compounds include, for example, benzyl trimethyl ammonium chloride, benzyl trimethyl ammonium bromide, tetrabutyl ammonium chloride, mixtures thereof and the like.

Suitable quaternary phosphonium compounds include those disclosed in U.S. Pat. No. 3,948,855 and U.S. Pat. No. 3,477,990 which are incorporated herein by reference.

Particularly suitable quaternary phosphonium compounds include, for example, methyl tributyl phosphonium dimethyl phosphate, benzyl triphenyl phosphonium chloride, methyl tri-n-butyl phosphonium bicarbonate, mixtures thereof and the like.

Suitable sulfonium compounds include, for example, tributyl sulfonium iodide, dimethyl isobutyl sulfonium chloride, n-amyl dimethyl sulfonium hydroxide, mixtures thereof and the like.

Suitable crown ethers include, for example, 18-Crown-6, 12-Crown-4, 15-Crown-5, mixtures thereof and the like.

These ethylenically unsaturated compounds can be polymerized with themselves or copolymerized with one or more materials containing at least one polymerizable ethylenically unsaturated group.

Suitable such materials containing at least one polymerizable unsaturated group include, for example, styrene, vinyl toluene, ortho-, meta- and parahalostyrenes, vinyl naphthalene, the various alpha-substituted styrenes, as well as the various di-, tri- and tetrahalo styrenes and acrylic, methacrylic and crotonic acid esters which include both the saturated alcohol esters and the hydroxyalkyl esters, mixtures thereof and the like.

The polymerization is conducted in the presence of free radical catalysts such as organic peroxides such as, for example, benzoyl peroxide, azobisisobutyronitrile, cumene hydroperoxide, mixtures thereof and the like.

Also, it may be desirable to include accelerators such as, for example, cobalt naphthenate, mixtures thereof and the like.

The usual epoxy resin curing agents can be employed to prepare cured compositions such as, for example, dicarboxylic acids, and anhydrides thereof, primary, secondary and tertiary amines, mixtures thereof and the like.

The epoxy resins can be employed in the preparation of structural or electrical laminates or composites, coatings, castings, potting, encapsulation, mixtures thereof and the like.

The following examples are illustrative of the present invention, but are not to be construed as to limiting the scope thereof.

EXAMPLE

Preparation of the diglycidyl ether of 3,5-dimethyl-1-hexyne-3-ol 63 g (0.5 mole) of 3,5-dimethyl-1-hexyne-3-ol was dissolved in 1000 ml epichlorohydrin. Tetrabutylammonium chloride (20 ml of 50% aqueous solution) was added. The mixture was stirred at 550 rpm and heated to 55° C., 200 ml of 50% aqueous sodium hydroxide (3.8 moles) was added and the reaction temperature maintained at 60° C. for 20 minutes (1200 s). The reaction mixture was then cooled to 35° C., ice water (200 ml) was then added with gentle mixing. After settling, the bottom aqueous layer was removed through the bottom takeoff valve. A second charge of caustic (200 ml) was then added and the mixture heated and stirred for 15 minutes (900 s) at 60° C. The workup procedure above was repeated and followed with a third and final caustic treatment. After the final caustic treatment, the 50% caustic was diluted with an equal volume of ice water and the mixture stirred for one hour (3600 s) at 30° C. to complete epoxidation of residual chlorohydrins. After the epoxidation step the aqueous layer was removed by the bottom valve and the organic layer washed with a solution of 5% $NaH_2PO_4$ to neutralize residual caustic. This was followed by a final wash with an equal volume of deionized water. The epichlorohydrin and volatile by-products were removed by vacuum evaporation in a rotary vacuum evaporator. The product was a mobile liquid. IR analysis indicated the absence of acetylenic triple bonds and the presence of C=C. NMR analysis showed the product to be a compound represented by the structure

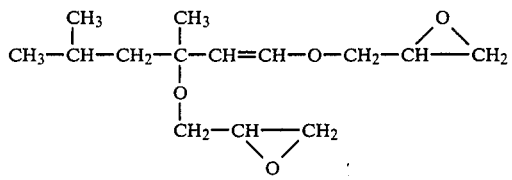

I claim:

1. A compound represented by the formula

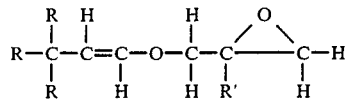

wherein each R is independently hydrogen, a hydrocarbyl group having from about 1 to about 12 carbon atoms, a glycidyl ether group or a glycidyl ether substituted hydrocarbyl group having from 4 to about 8 carbon atoms or two of such R groups can be combined to form a cyclic structure and wherein R' is hydrogen or an alkyl group having from 1 to about 3 carbon atoms.

2. A compound of claim 1 wherein when R is a hydrocarbyl group or a hydroxyl substituted hydrocarbyl group such hydrocarbyl groups contain from 1 to about 6 carbon atoms and R' is hydrogen.

3. A compound of claim 2 which is a diglycidyl ether derived from 3,5-dimethyl-1-hexyne-3-ol.

4. The product of product mixture which results from dehydrohalogenating the product or mixture of products resulting from reacting (A) at least one material represented by the formula

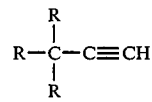

wherein each R is independently hydrogen, a hydrocarbyl group having from 1 to about 12 carbon atoms, a hydroxyl substituted hydrocarbyl group having from about 1 to about 12 carbon atoms or two of such R groups can be combined to form a cyclic structure;

(B) at least one material represented by the formula

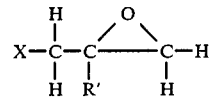

wherein R' is hydrogen or an alkyl group having from 1 to about 3 carbon atoms and X is a halogen; wherein components (A) and (B) are employed in quantities which provide from about 1 to about 20 moles of component (B) for each hydroxyl and —C≡CH group contained in component (A).

5. The product or product mixture of claim 4 wherein when R is a hydrocarbyl group or a hydroxyl substituted hydrocarbyl group such hydrocarbyl groups contain from 1 to about 12 carbon atoms and R' is hydrogen.

6. The product or product mixture of claim 5 wherein component (A) is 3,5-dimethyl-1-hexyne-3-ol.

* * * * *